United States Patent [19]

Ackermann et al.

[11] 4,349,567
[45] Sep. 14, 1982

[54] DIHALOVINYLCYCLOPROPANECARBOXYLIC ACID ESTERS AND THEIR USE IN PEST CONTROL

[75] Inventors: Peter Ackermann, Reinach; Jozef Drabek, Oberwil; Saleem Farooq, Ettingen; Laurenz Gsell, Basel; Odd Kristiansen, Möhlin; Rudolf Wehrli, Rheinfelden, all of Switzerland

[73] Assignee: Ciba-Geigy Corporation, Ardsley, N.Y.

[21] Appl. No.: 174,984

[22] Filed: Aug. 4, 1980

[30] Foreign Application Priority Data

Aug. 16, 1979 [CH] Switzerland .................. 7513/79
Mar. 18, 1980 [CH] Switzerland .................. 2120/80
Jun. 20, 1980 [CH] Switzerland .................. 4750/80

[51] Int. Cl.³ .................. A01N 53/00; C07C 69/743; C07C 69/747
[52] U.S. Cl. .................. 424/305; 560/124; 568/637; 424/306
[58] Field of Search .................. 560/124; 424/305

[56] References Cited

U.S. PATENT DOCUMENTS 4,024,163  5/1977  Elliott .................. 560/124

*Primary Examiner*—Michael Shippen
*Attorney, Agent, or Firm*—Frederick H. Rabin

[57] ABSTRACT

Cyclopropanecarboxylic acid esters of the formula

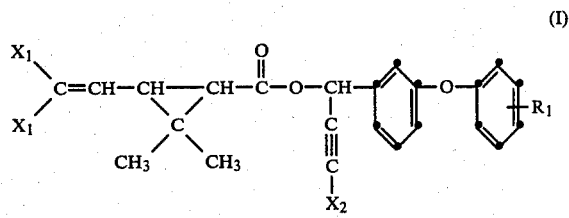

wherein $R_1$ is hydrogen, halogen, methyl, trifluoromethyl or methoxy, and $X_1$ and $X_2$ are each halogen.

A process for producing the above compounds and their use in pest control, as well as α-haloethynyl-3-phenoxy-benzyl alcohols.

8 Claims, No Drawings

DIHALOVINYLCYCLOPROPANECARBOXYLIC ACID ESTERS AND THEIR USE IN PEST CONTROL

The present invention relates to dihalovinylcyclopropanecarboxylic acid esters, to processes for producing them, and to their use in pest control, and also to α-haloethynyl-3-phenoxy-benzyl alcohols.

The dihalovinylcyclopropanecarboxylic acid esters have the formula

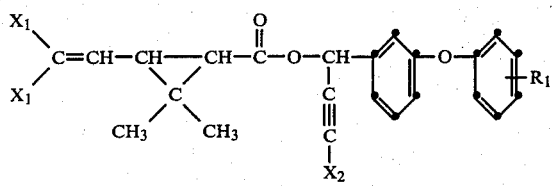
(I)

wherein $R_1$ is hydrogen, halogen, methyl, trifluoromethyl or methoxy, and $X_1$ and $X_2$ are each halogen.

By halogen is meant fluorine, chlorine, bromine or iodine.

Compounds of the formula I preferred on account of their action are those wherein $R_1$ is hydrogen, fluorine, chlorine, methyl or trifluoromethyl, $X_1$ is fluorine, chlorine or bromine, and $X_2$ is bromine or iodine.

Particularly preferred compounds of the formula I are those wherein $R_1$ is hydrogen or fluorine, $X_1$ is chlorine and $X_2$ is bromine or iodine.

The compounds of the formula I are produced by methods known per se, for example as follows:

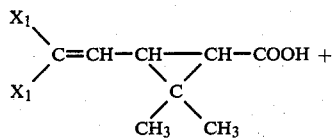
(II)

(1)

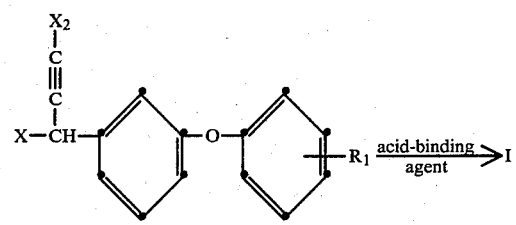
(III)

acid-binding agent → I

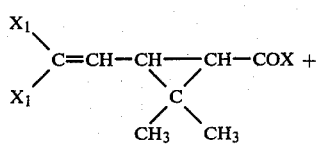
(IV)

(2)

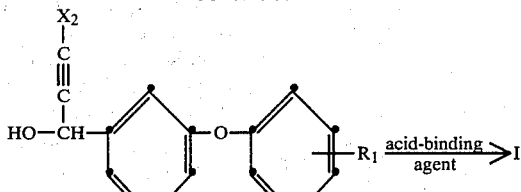
(V)

acid-binding agent → I (3)

$$X_1\!\!\diagdown\!\!\!\!\!\!{\phantom{X}}\atop X_1\!\!\diagup\!\!\!{\phantom{X}}\!\!C\!\!=\!\!CH\!-\!CH\!\!\!\underset{\underset{\displaystyle CH_3\ \ CH_3}{\diagdown\diagup}}{\overset{\displaystyle\phantom{C}}{\phantom{C}}}\!\!\!CH\!-\!COOH\ +$$

(II)

HO—CH—[Ar]—O—[Ar]—$R_1$   water-binding agent → I (V)

(4)

$$X_1\!\!\diagdown\!\!\!\!\!\!{\phantom{X}}\atop X_1\!\!\diagup\!\!\!{\phantom{X}}\!\!C\!\!=\!\!CH\!-\!CH\!\!\!\underset{\underset{\displaystyle CH_3\ \ CH_3}{\diagdown\diagup}}{\overset{\displaystyle\phantom{C}}{\phantom{C}}}\!\!\!CH\!-\!COOR\ +$$

(VI)

HO—CH—[Ar]—O—[Ar]—$R_1$   —ROH → I.

(V)

In the formulae II to VI, the symbols $R_1$, $X_1$ and $X_2$ have the meanings given under the formula I.

X in the formulae III and IV is a halogen atom, particularly chlorine or bromine, and R in the formula VI is $C_1$–$C_4$-alkyl, especially methyl or ethyl. Suitable as acid-binding agents for the processes 1 and 2 are in particular tertiary amines, such as trialkylamine and pyridine, also hydroxides, oxides, carbonates and bicarbonates of alkali metals and alkaline-earth metals, as well as alkali metal alcoholates, for example potassium-tert-butylate and sodium methylate. The water-binding agent for the process 3 can be for example dicyclohexylcarbodiimide. The processes 1 to 4 are performed at a reaction temperature of between −10° and 120° C., usually between 20° and 80° C., under normal or elevated pressure, and preferably in an inert solvent or diluent. Suitable solvents or diluentes are for example: ethers and ethereal compounds, such as diethyl ether, dipropyl ether, dioxane, dimethoxyethane and tetrahydrofuran; amides, such as dialkylated carboxylic acid amides; aliphatic, aromatic as well as halogenated hydrocarbons, especially benzene, toluene, xylenes, chloroform and chlorobenzene; nitriles, such as acetonitrile; dimethyl sulfoxide, and ketones, such as acetone and methyl ethyl ketone.

The starting materials of the formulae II, IV and VI are known, or can be produced by methods analogous to known methods. The starting materials of the formulae III and V are novel. They are produced for example by a process analogous to that described in Tetrahedron Letters, Vol. 34, pp 1449–1452 (1978) (cp. also Example 1A).

The compounds of the formula I occur as mixtures of various optically active isomers unless homogeneous optically active starting materials are used in the production process. The different isomeric mixtures can be separated by known methods into the individual isomers. By the term 'compound of the formula I' are meant both the individual isomers and the mixtures thereof.

The compounds of the formula I are suitable for combating various animal and plant pests. They are suitable in particular for controlling insects and phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

Compounds of the formula I are especially suitable for combating insects which damage plants, particularly insects which damage plants by eating, in crops of ornamental plants and productive plants, especially in cotton crops (for example against Spodoptera littoralis and Heliothis virescens), and in crops of vegetables (for example against *Leptinotarsa decemlineata* and *Myzus persicae*). The active substances of the formula I also exhibit a very favourable action against flies, such as Musca domestica, and against mosquito larvae.

The compounds of the formula I exhibit also a very good action against keratin-eating Lepidoptera, for example Tineola spec. and Tinea spec., and also against keratin-eating Coleoptera, for example Anthrenus spec. and Attagenus spec. The compounds are therefore very well suited for protecting keratinous materials against infestation by pests. The compounds of the formula I can be applied by processes customarily used for textile finishing, and are therefore excellently suitable for protecting keratinous materials against damage caused by insects eating, especially for imparting to such materials a finish fast to washing and to light. The said materials can be treated both in the crude state and in the processed state, and they can be for example crude or processed sheep wool, and products from other kinds of animal hair, and from pelts, furs and feathers. In addition to being used to impart a finish fast to light and to washing, in the dye bath and in the padding process, the compounds of the formula I can be used also for the impregnation of wool and woollen articles during dry cleaning, by which means likewise an excellent protection against damage by insects is achieved.

The compounds of the formula I exhibit, besides an insecticidal activity against the larvae of the clothes moth (*Tineola bisselliela*) and against the pelt moth (*Tinea pellionella*), an insecticidal activity also against the larvae of the black carpet beetle and carpet beetle (Atteagenus spec. and Anthrenus spec.). The textiles treated in the chosen manner with the compounds according to the invention, for instance materials such as wool blankets, wool carpets, wool scouring, wool clothing and knitted goods, are therefore protected against the common keratin-eating insects. To be mentioned among the materials to be protected are also mixed fabrics of which one of the components is wool. They may be mixed fabrics of wool with other natural fibres, such as cotton, and with artificial fibres.

The compositions used to protect keratinous materials against damage caused by insects should contain the active substances of the formula I in dissolved or finely divided form. The forms applied are therefore solutions, suspensions and emulsions of active substances.

By virtue of their good solubility in organic solvents, the compounds of the formula I are particularly suitable also for application from non-aqueous media. The materials to be protected can simply be impregnated with these solutions, or it is possible, by suitable choice of solvent, to combine the process for imparting a mothproof and beetleproof finish with a dry cleaning process.

Organic solvents which have proved particularly satisfactory are propylene glycol, methoxyethanol, ethoxyethanol and dimethylformamide, to which can be added distributing agents and/or other auxiliaries. Mentioned as distributing agents are emulsifiers, for example sulfonated castor oil, sulfite waste liquor and fatty alcohol sulfates.

The compounds of the formula I are also excellently suitable for spray application, since they are very readily soluble in the volatile organic solvents customarily used. Suitable materials for spray application are in particular wool-containing textiles, pelts and feathers.

To be especially emphasised are methods of application such as padding, impregnating and spraying with volatile organic solvents, because waste-water contamination is avoided on account of the recovery of these solvents.

The acaricidal and insecticidal action can be substantially broadened and adapted to suit given circumstances by the addition of other insecticides and/or acaricides. Suitable additives are for example: organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances having a synergistic or intensifying effect on pyrethroids. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane, S,S,S-tributylphosphorotrithioates and 1,2-methylenedioxy-4-(2-(octylsulfinyl)-propyl)-benzene.

Compounds of the formula I can be used on their own or together with suitable carriers and/or additives. Suitable carriers and additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations: dusts, scattering agents, granules (coated granules, impregnated granules and homogeneous granules);

liquid preparations:
(a) water-dispersible concentrates of active substance: wettable powders, pastes or emulsions;
(b) solutions.

The content of active substance in the compositions described above is between 0.1 and 95%; it is to be mentioned in this respect that with application from an aeroplane, or from other suitable devices, concentrations of up to 99.5% or even the pure active substance can be used.

The active substances of the formula I can be formulated for example as follows (parts are by weight).

Dusts

The following substances are used to produce (a) a 5% dust and (b) a 2% dust:
(a)
  5 parts of active substance, and
  95 parts of talcum; and
(b)
  2 parts of active substance,
  1 part of highly dispersed silicic acid, and
  97 parts of talcum.

The active substance is mixed and ground with the carriers.

Granulate

The following ingredients are used to produce a 5% granulate:
  5 parts of active substance,
  0.25 part of epoxidised vegetable oil,
  0.25 part of cetyl polyglycol ether,
  3.50 parts of polyethylene glycol, and
  91 parts of kaolin (particle size 0.3–0.8 mm).

The active substance is mixed with epoxidised vegetable oil, and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:
(a)
  40 parts of active substance,
  5 parts of sodium lignin sulfonate,
  1 part of sodium dibutyl-naphthalene sulfonate, and
  54 parts of silicic acid;
(b)
  25 parts of active substance,
  4.5 parts of calcium lignin sulfonate,
  1.9 parts of Champagne chalk/hydroxyethyl cellulose mixture (1:1),
  1.5 parts of sodium dibutyl-naphthalene sulfonate,
  19.5 parts of silicic acid,
  19.5 parts of Champagne chalk, and
  28.1 parts of kaolin;
(c)
  25 parts of active substance,
  2.5 parts of isooctylphenoxy-polyoxyethylene-ethanol,
  1.7 parts of Champagne chalk/hydroxyethyl cellulose mixture (1:1),
  8.3 parts of sodium aluminum silicate,
  16.5 parts of kieselguhr, and
  46 parts of kaolin; and
(d)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:
(a)
  10 parts of active substance,
  3.4 parts of epoxidised vegetable oil,
  3.4 parts of a combination emulsifier consisting of fatty alcohol polyglycol ether and alkylarylsulfonate calcium salt,
  40 parts of dimethylformamide, and
  43.2 parts of xylene;
(b)
  25 parts of active substance,
  2.5 parts of epoxidised vegetable oil,
  10 parts of alkylarylsulfonate/fatty alcohol polyglycol ether mixture,
  5 parts of dimethylformamide, and
  57.5 parts of xylene; and
(c)
  50 parts of active substance,
  4.2 parts of tributylphenol-polyglycol ether,
  5.8 parts of calcium-dodecylbenzenesulfonate,
  20 parts of cyclohexanone, and
  20 parts of xylene.

Emulsions of the required concentration can be prepared from these concentrates by dilution with water.

Sprays

The following constituents are used to produce (a) a 5% spray and (b) a 95% spray:
(a)
  5 parts of active substance,
  1 part of epoxidised vegetable oil, and
  94 parts of ligroin (boiling limits 160°–190° C.); and
(b)
  95 parts of active substance, and
  5 parts of epoxidised vegetable oil.

The invention is further illustrated by the Examples which follow:

EXAMPLE 1

(A) 0.1 mol of methyl lithium dissolved in 50 ml of ether is added dropwise within 20 minutes under argon, at −50° to −60° C., to 10 g of α-ethynyl-m-phenoxybenzyl alcohol in 500 ml of ether. After a further 10 minutes, 5.63 g of iodine dissolved in 100 ml of ether are added dropwise, and the mixture is stirred at room temperature for 10 hours. There are then slowly added dropwise 2 ml of isopropanol, and subsequently 20 ml of saturated ammonium chloride solution are added. The ether phase is washed with saturated sodium chloride solution and dried over magnesium sulfate. After removal of the solvent, the residue is chromatographed on silica gel by means of ether/hexane (1:2). There is obtained the compound of the formula

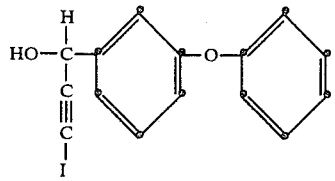

NMR spectrum (60 MHz) in CDCl$_3$/TMS n$_D^{20°}$ = 1.6237,
δ3.1: d 1H
δ5.4: d 1H
δ6.7–7.7: m 9H.

The following compounds are prepared in an analogous manner:

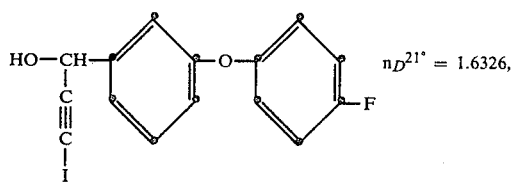
n$_D^{21°}$ = 1.6326,

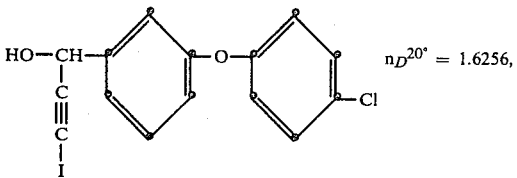
n$_D^{20°}$ = 1.6256,

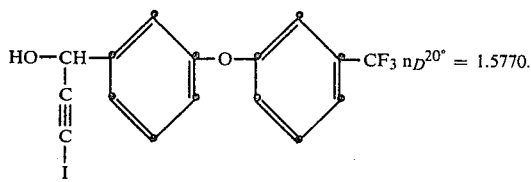
n$_D^{20°}$ = 1.5770.

(B) Production of α-iodoethynyl-3-phenoxybenzyl-2,2-dimethyl-3-(2',2'-dichlorovinyl)-cyclopropane-1-carboxylate A solution of 4.1 g of α-iodoethynyl-m-phenoxybenzyl alcohol in 20 ml of toluene is added dropwise to an ice-cooled solution of 2.63 g of 2,2-dimethyl-3-(2',2'-dichlorovinyl)-cyclopropanecarboxylic acid chloride and 1.2 ml of pyridine in 50 ml of toluene. The reaction mixture is stirred under nitrogen for 16 hours at room temperature, and ether is then added. The ether extract is washed once with water, once with 2 N hydrochloric acid and three times with saturated sodium chloride solution; it is subsequently dried over sodium sulfate, filtered and concentrated by evaporation. The product is chromatographed through silica gel with ether/hexane (1:10) as the eluant.

There is obtained the compound of the formula

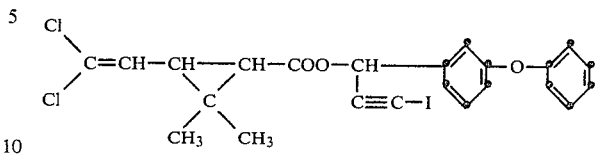

with a refractive index of n$_D^{20}$ = 1.5913, NMR spectrum (60 MHz) in CDCl$_3$TMS
δ6.9–7.6: m 9H
δ6.5 and 6.53: s 1H
δ6.3: d 1H
δ1.8–2.2: m 2H
δ1.1–1.4: m 6H.

The following compounds are produced in an analogous manner:

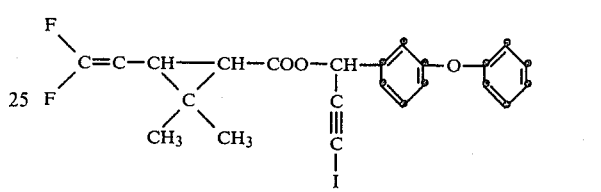
n$_D^{20}$ = 1.5630,

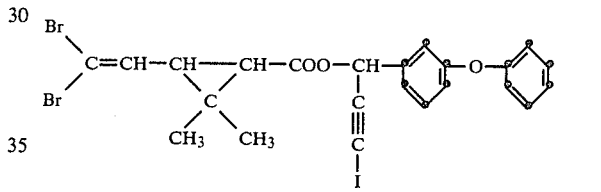
n$_D^{20}$ = 1.5895,

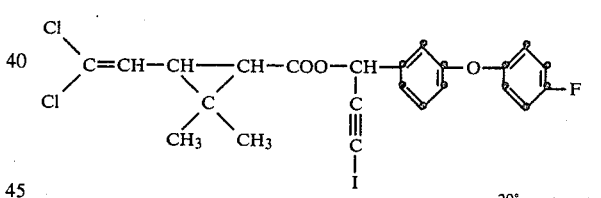
n$_D^{20°}$ = 1.5765,

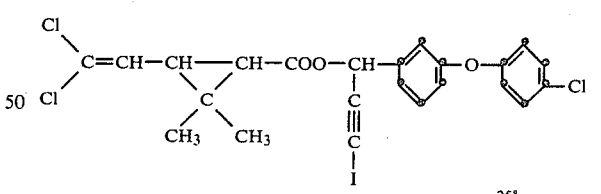
n$_D^{25°}$ = 1.5925,

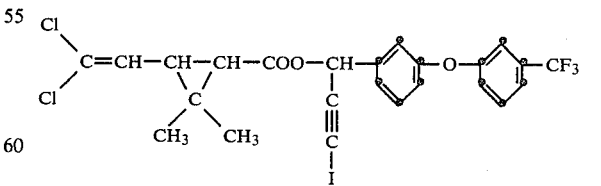
n$_D^{20°}$ = 1.5643.

(C) Production of α-bromoethynyl-3-phenoxy-benzyl alcohol

I. Production of tetrahydropyranyl ether of α-ethynyl-3-phenoxybenzyl alcohol. A solution of 5 g of α- ethynyl-3-phenoxybenzyl alcohol, 2.3 g of 3,4-dihydro-2-H-pyrane in 20 ml of hexane and 5 ml of toluene are added dropwise to a suspension of 0.8 g of Amberlyst H-15 in 20 ml of hexane. The mixture is stirred for one hour at 20° C.; the catalyst is subsequently distilled off, and the solvent is removed under reduced pressure. There is obtained the compound of the formula

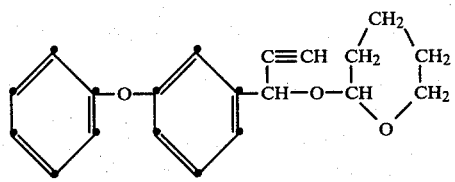

with a refractive index of $n_D^{20°} = 1.5481$. (Lit.: A. Bougini et al.; Synthesis 1979, 618–620).

II. Production of tetrahydropyranyl ether of α-bromoethynyl-3-phenoxybenzyl alcohol: 35 g of tetrahydropyranyl ether of α-ethynyl-3-phenoxybenzyl alcohol are dissolved in 450 ml of hexane; the solution is added to a solution of 132 g of bromine, 315 g of sodium hydroxide and 1 g of tetrabutylammonium bromide in 1400 ml of water, and the whole is then stirred at 20° C. for 72 hours. To the reaction mixture are again added 132 g of bromine, and stirring is maintained for a further 24 hours at 20° C.; the organic phase is separated, and the aqueous phase is extracted twice with 300 ml of hexane each time. The combined organic phases are washed with 3×500 ml of saturated sodium chloride solution, dried over magnesium sulfate, and concentrated under reduced pressure. The crude product is filtered through silica gel with an ether/hexane (1:10) solution. There is thus obtained the compound of the formula

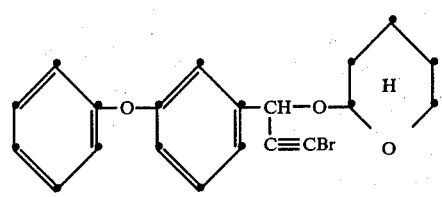

having a refractive index of $n_D^{20°} = 1.5932$.

III. Production of α-bromoethynyl-3-phenoxy-benzyl alcohol: 30 g of tetrahydropyranyl ether of α-bromoethynyl-3-phenoxybenzyl alcohol are stirred for 90 minutes at 45° C. with 230 ml of methanol and 2.3 g of Amberlyst H-15. The reaction mixture is filtered, and the residue is concentrated under reduced pressure. The crude product is chromatographed through silica gel with an ether/hexane (1:2) solution as the eluant to yield the compound of the formula

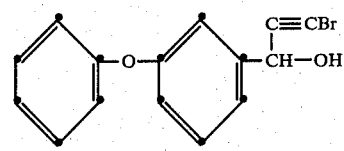

having a refractive index of $n_D^{20°} = 1.6191$.

The following compounds are produced in an analogous manner:

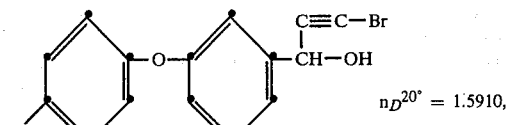

$n_D^{20°} = 1.5910$,

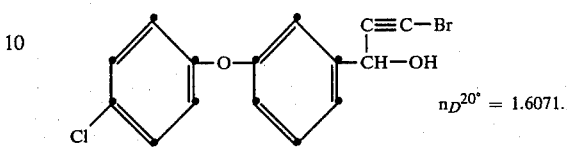

$n_D^{20°} = 1.6071$.

(D) Production of α-bromoethynyl-3-phenoxy-benzyl-2,2-dimethyl-2-(2',2'-dichlorovinyl)-cyclopropanecarboxylate A solution of 3.55 g of α-bromoethynyl-m-phenoxybenzyl alcohol in 20 ml of toluene is added dropwise to an ice-cooled solution of 2.63 g of 2,2-dimethyl-3-(2',2'-dichlorovinyl)-cyclopropanecarboxylic acid chloride and 1.2 ml of pyridine in 50 ml of toluene. The reaction mixture is stirred under nitrogen for 16 hours at room temperature, and ether is then added. The ether extract is washed once with water, once with 2 N hydrochloric acid and three times with saturated sodium chloride solution; it is subsequently dried over sodium sulfate, filtered, and concentrated by evaporation. The product is chromatographed through silica gel with ether/hexane (1:10) as the eluant. There is obtained the compound of the formula

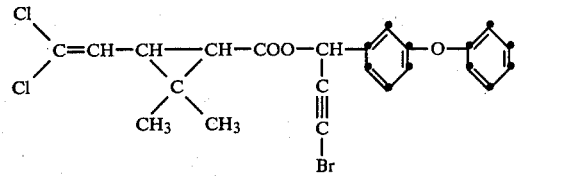

having a refractive index of $n_D^{20°} = 1.5772$.

The following compounds are produced in an analogous manner:

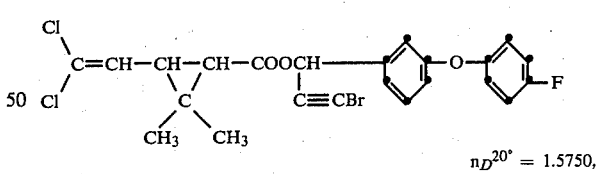

$n_D^{20°} = 1.5750$,

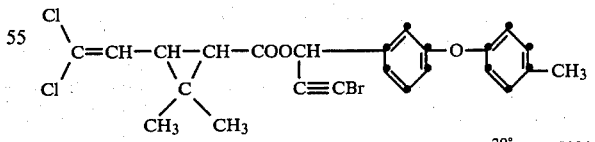

$n_D^{20°} = 1.5821$.

EXAMPLE 2

Insecticidal stomach-poison action

Cotton plants were sprayed with a 0.5% aqueous active-substance solution. After the drying of the coating, larvae of *Spodoptera littoralis* in the $L_3$ stage and of Heliothis virescens in the $L_3$ stage were settled onto the cotton plants. The test was carried out at 24° C. with 60% relative humidity.

Compounds of the formula I according to Example 1 exhibited at the given concentration a 100% insecticidal stomach-poison action against *Spodoptera littoralis* and *Heliothis virescens* larvae.

EXAMPLE 3

Acaricidal action

*Phaseolus vulgaris* plants were infested, 12 hours before the test for acaricidal action, with an infested piece of leaf from a mass culture of *Tetranychus urticae*. The transferred mobile stages were sprayed with solutions containing 100, 200, 400 and 800 ppm, respectively, of the test preparations, from a chromatography-sprayer in a manner ensuring no overflow of the spray-liquor. An assessment was made after 2 and 7 days, by examination under a binocular microscope, of the living larvae and of the dead larvae, adults and eggs, and the results were expressed as percentages. The treated plants were kept during the "holding time" in greenhouse compartments at 25° C.

Within the given concentrations, compounds of the formula I were 100% effective against adults, larvae and eggs of *Tetranychus urticae*.

EXAMPLE 4

(a) *Rhipicephalus bursa*

For each concentration, 5 adult ticks and 50 tick larvae, respectively, were counted into a small glass test tube, and immersed for 1 to 2 minutes in 2 ml of an aqueous solution from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults were made after 2 weeks and in the case of the larvae after 2 days. There were two repeats for each test.

(b) *Boophilus microplus* (larvae)

With a dilution series analogous to that of Test (a), tests were carried out with 20 sensitive larvae and OP-resistant larvae, respectively (resistance is with respect to diazinon compatibility).

Within the given concentration limits, compounds of the formula I according to Example 1 were 100% effective in these tests against adults and larvae of Rhipicephalus bursa and against sensitive and OP-resistant larvae, respectively, of Boophilus microplus.

EXAMPLE 5

Insecticidal contact action: *Aphis craccivora* and *Myzus persicae*

Plants (*Vicia faba*) grown in pots were each infested before commencement of the test with about 200 individuals of the species *Aphis craccivora* and *Myzus persicae*, respectively. The plants treated in this manner were sprayed dripping wet 24 hours later with solutions containing 200 and 100 ppm, respectively, of the compound to be tested. Two plants were used per test compound and per concentration, and an evaluation of the mortality rate achieved was made after a further 24 hours.

Within the given concentration limits, compounds according to Example 1 exhibited a 100% action against insects of the species Aphis craccivora and Myzus persicae.

EXAMPLE 6

Exhaust method

There was prepared in each case a 0.4% stock solution in methyl cellosolve of one of the compounds according to Example 1. There was then prepared at room temperature an aqueous application liquor containing, in 120 ml of distilled water, 0.12 ml of "Sandozin KB" ®, 0.6 ml of formic acid 1:10 and 0.75 ml of the respective 0.4% stock solution. 3 g of a wool-flannel fabric was then soaked with hot water, and introduced into the liquor at room temperature. Whilst the wool sample was being continuously turned, the bath temperature was raised within 20 minutes to 60° C., and the sample was treated at 60° C. for 30 minutes. The bath was then cooled; the wool sample was subsequently rinsed twice for 3 minutes with distilled water, squeezed out by hand and dried in air. The concentration of active substance was 1000 ppm, calculated relative to the weight of wool.

The dried sample was subjected to the mothproofing test (moth-damage protection against the clothes moth *Tineola bisiella* Hum.), with application of the test for resistance to the larvae of the black carpet beetle (*Attagenus piceus* Ol.) and carpet beetle (*Anthrenus vorax* Wat.), according to SNV 195902.

For the tests there were used in each case larvae of Anthrenus vorax and 6- to 7-week-old larvae of *Attagenus piceus*. Pieces of individual size were cut from the treated wool-flannel samples, and subsequently exposed for 14 days, at constant temperature (28° C.) and constant relative humidity (65%), to attack (moth damage) from 15 larvae of the respective pests. The evaluation was made on the one hand on the basis of the relative loss of weight of the specimen, and on the other hand on the basis of the number of organisms still living.

The tested compounds according to Example 1 exhibited a very good action against the three genera of pests used in the tests.

EXAMPLE 7

Padding method

There was prepared in each case a 0.4% stock solution in methyl cellosolve of one of the compounds according to Example 1. 12.5 ml of the respective stock solution was diluted to 50 ml with methyl cellosolve containing per liter 0.65 g of "Sandozin KB" ® (solution No. 1). 24 ml of solution No. 1 was diluted to 50 ml with methyl cellosolve containing per liter 0.5 g of "Sandozin KB" ® (solution No. 2). 25 ml of solution No. 2 in its turn was diluted to 50 ml with methyl cellosolve containing per liter 0.5 g of "Sandozin KB" ® (solution No. 3). 3 ml of each of the solutions Nos. 1, 2 and 3 was placed into crystallising dishes, and a baited wool-flannel disc was wetted in each of the dishes for 3 seconds. The moist discs were then padded between aluminium sheets in such a manner that the squeezed discs had each absorbed 50% of liquor. The concentrations of active substance were then in turn 500 ppm, 250 ppm and 125 ppm for the treated discs from the solutions Nos. 1, 2 and 3, respectively. The moist discs were then dried in air, and subsequently subjected to the same biological tests as those described in Example 6.

The tested compounds according to Example 1 exhibited a very good action against all three genera of pests, even at the lowest concentration of 125 ppm.

What is claimed is:

1. A cyclopropanecarboxylic acid ester of the formula

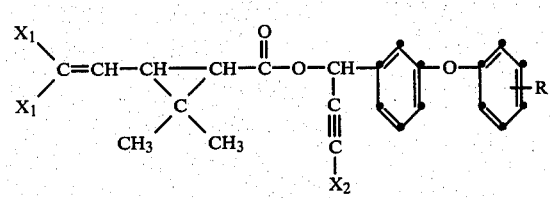

wherein $R_1$ is hydrogen, halogen, methyl, trifluoromethyl or methoxy, and $X_1$ and $X_2$ are each halogen.

2. A compound according to claim 1, wherein $R_1$ is hydrogen, fluorine, chlorine, methyl or trifluoromethyl, $X_1$ is fluorine, chlorine or bromine, and $X_2$ is bromine or iodine.

3. A compound according to claim 2, wherein $R_1$ is hydrogen or fluorine and $X_1$ is chlorine.

4. The compound according to claim 3 of the formula

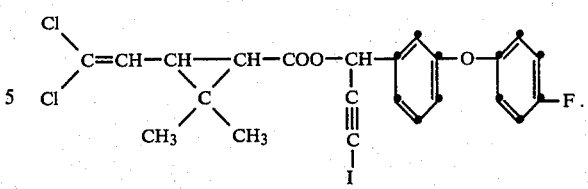

5. The compound according to claim 3 of the formula

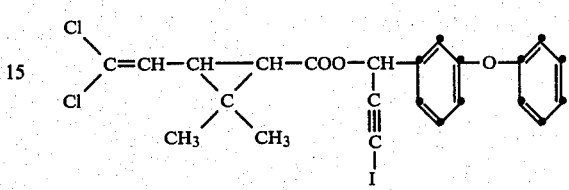

6. The compound according to claim 3 of the formula

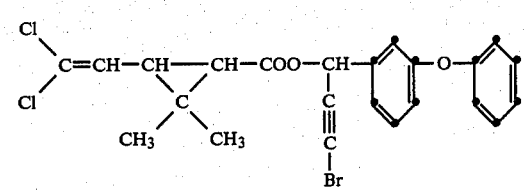

7. An insecticidal or acaricidal composition containing as active ingredient an insecticidally or acaricidally effective amount of a compound according to claim 1, together with suitable carriers.

8. A method of combating insects and acarids which comprising applying to the locus thereof an insecticidally or acaricidally effective amount of a compound according to claim 1.

* * * * *